US005762903A

United States Patent [19]
Park et al.

[11] Patent Number: 5,762,903
[45] Date of Patent: Jun. 9, 1998

[54] RADIOACTIVE CHITOSAN COMPLEX FOR RADIATION THERAPY

[75] Inventors: Kyoung Bae Park; Young-Mi Kim; Jae-Rock Kim, all of Seoul, Rep. of Korea

[73] Assignee: Korea Atomic Energy Research Institute, Daejeon-Si, Rep. of Korea

[21] Appl. No.: 612,662

[22] Filed: Mar. 8, 1996

Related U.S. Application Data

[63] Continuation-in-part of Ser. No. 471,516, Jun. 6, 1995, abandoned.

[30] Foreign Application Priority Data

Mar. 10, 1995 [KR] Rep. of Korea .................... 95-4872
Feb. 28, 1996 [KR] Rep. of Korea .................... 96-5038

[51] Int. Cl.$^6$ ............... A61K 51/12; A61K 51/06; A61N 5/00
[52] U.S. Cl. ............... 424/1.29; 424/1.33; 424/1.65; 424/1.73; 600/3
[58] Field of Search ............... 424/1.33, 1.29, 424/1.25, 1.37, 1.65, 1.73; 514/55, 917; 536/20; 600/3; 252/625, 634

[56] References Cited

U.S. PATENT DOCUMENTS

| 4,424,346 | 1/1984 | Hall et al. .................... 536/20 |
| 4,946,435 | 8/1990 | Suthanthiran et al. . |
| 5,219,749 | 6/1993 | Bouriotis et al. .................... 435/227 |
| 5,268,129 | 12/1993 | Simon et al. .................... 252/644 |
| 5,271,924 | 12/1993 | Hashiguchi et al. .................... 424/9 |
| 5,300,280 | 4/1994 | DeRosch et al. .................... 424/1.53 |
| 5,342,283 | 8/1994 | Good . |
| 5,364,613 | 11/1994 | Sieving et al. .................... 424/9 |
| 5,422,116 | 6/1995 | Yen et al. .................... 424/427 |

FOREIGN PATENT DOCUMENTS

WO91/09622  7/1991  WIPO .

OTHER PUBLICATIONS

Andrews et al., "Hepatic Radioembolization with Yttrium–90 Containing Glass Microspheres: Preliminary Results and Clinical Follow–up", Journal of Nuclear Medecine 1994, vol. 35, pp. 1637–1646.

Mumper et al., "Neutron–Activated Holmium–166–Poly (L–Lactic Acid) Microspheres: A Potential Agent for the Internal Radiation Therapy of Hepatic Tumors", Journal of Nuclear Medicine 1991, vol. 32, pp. 2139–2143.

Will et al., "Comparison of Two Yttrium–90 Regimens in Inflammatory and Osteoarthropathics", Annals of the Rheumatic Diseases 1992, vol. 51, pp. 262–265.

Chinol et al., "Chemistry and Biological Behavior of Samarium–153 and Rhenium–186–Labeled Hydroxyapatite Particles: Potential Radiopharmaceuticals for Radiation Synovectomy", Journal of Nuclear Medicine, 1993, vol. 34, pp. 1536–1542.

Knorr, "Functional Properties of Chitin and Chitosan", Journal of Food Science 1982, vol. 47, pp. 593–595.

Hnatowich et al., "Dysprosium–165 Ferric Hydroxide Macroaggregates for Radiation Synovectomy", Journal of Nuclear Medecine 1977, vol. 19, No. 3, pp. 303–308.

Wang et al. "Preparation and Biodistribution of Yttrium–90 Lipiodolin Rats Following Hepatic Arterial Injection", European Journal of Nuclear Medicine, Mar. 1995, vol. 22, No. 3, pp. 233–236.

McLaren et al., "Dysprosium ($^{165}$Dy) Hydroxide Macroaggregates for Radiation Synovectomy–Animal Studies", European Journal of Nuclear Medicine 1990, vol. 16, pp. 627–632.

Clunie et al., "Samarium–153–Particulate Hydroxyapatite Radiation Synovectomy: Biodistribution Data for Chronic Knee Synovitis", Journal of Nuclear Medicine 1995, vol. 36, pp. 51–57.

Chemical Abstracts, vol. 123, No. 16, 16 Oct. 1995, Abstract No. 217120.

Chemical Abstracts, vol. 108, No. 1, 4 Jan. 1988, Abstract No. 1631.

Chemical Abstracts, vol. 124, Abstract No. 311363, Jan. 1996.

Patent Abstracts of Japan, vol. 13, No. 516 (C–656), 17 Nov. 1989.

*Primary Examiner*—Gary E. Hollinden
*Assistant Examiner*—Michael G. Hartley
*Attorney, Agent, or Firm*—Dilworth & Barrese

[57] ABSTRACT

The present invention relates to the radioactive chitosan complex formed by labelling a chitosan, a biocompatible and biodegradable natural polymer, with radionuclide, a radioactive chitosan macroaggregate formed by making chitosan complex into particles, and a kit for preparing radioactive chitosan complex, process for preparation thereof and the use thereof for an internal radiation therapeutic agent. The radioactive chitosan complex and its macroaggregate can be used as an internal radiation therapy for rheumatoid arthritis or cystic cancer such as liver cancer, brain cancer, breast cancer, ovary cancer and the like by administering them directly to the lesion.

19 Claims, No Drawings

5,762,903

1

RADIOACTIVE CHITOSAN COMPLEX FOR RADIATION THERAPY

This is a continuation-in-part of application Ser. No. 08/471,516 filed Jun. 6, 1995, now abandoned.

FIELD OF THE INVENTION

The present invention relates to a radioactive chitosan complex, its macroaggregate and a kit for preparing radioactive chitosan complex, process for preparation thereof, and the use thereof for radiation therapy.

In particular, the present invention relates to a radioactive chitosan complex formed by labelling chitosan with radionuclides, and radioactive chitosan macroaggregate formed by making chitosan complex into particles, and a kit for preparing radioactive chitosan complex.

The present invention relates to the process for preparation of radioactive chitosan complex by reacting radionuclide solution with chitosan solution, and the process for preparation of radioactive chitosan macroaggregate by adding alkaline solution to radioactive chitosan complex.

In addition, the present invention relates to the use of radioactive chitosan complex and its macroaggregate for internal radiation therapy that lesions are treated with radiation emitted from the radioactive materials administered directly to lesions.

BACKGROUND OF ART

There are two kinds of radiation therapy, one is an external radiation therapy that lesions are treated with radiation irradiated from the outside of the body, and the other is an internal radiation therapy that lesions are treated with radiation irradiated from the administered radioactive materials in the body.

Hitherto the external radiation therapy has been widely used, but it causes the problem that normal tissue or organs are irradiated and damaged, since strong radiation should be used in order to reach the lesion.

Therefore, the internal radiation therapy that only the lesion where the radioactive materials are directly administered is irradiated has been developed.

In the internal therapy, since the radiation are emitted in the lesion, the radioactive materials of weak potency can be used, and hence only lesions are irradiated and other organs can be protected from irradiation.

Recently the internal radiation therapy has been widely applied on account of its excellent effect.

The representative diseases treated by the internal radiation therapy are cancers and rheumatoid arthritis.

The method of treatment for cancers or rheumatoid arthritis can be largely classified to a medicinal treatment, a surgical treatment and a radiation treatment. But the medicinal and radiation treatment have been widely prevailed. As known from the report that only 5% of the liver cancers can be treated by the surgical treatment, a surgical treatment has not often been utilized.

In case that the anti-cancer drugs are administered orally or intravenously, it is needed that the large quantity of the drugs should be administered, since the medicine is spread to the whole body through a blood flow and only a little amount is accumulated in lesion, and resultantly adverse effect is raised.

Recently radiation therapy, especially the internal radiation therapy for cancers and arthritis, has been widely utilized.

For instance, hepatic artery method based on the fact that hepatoma cells take nutrition through hepatic artery and normal hepatic cells through hepatic vein is that radioactive materials labelled radionuclide is directly injected into hepatic artery instead of intravenous injection to block hepatoma cell's taking the nutrition and to accumulate more radioactive materials in hepatoma cells.

The internal radiation therapy has been also used for rheumatoid arthritis as well as cystic cancers such as hepatoma, brain tumor, breast tumor, ovary tumor and the like.

In a treatment of rheumatoid arthritis, a surgical synovectomy or radiation synovectomy may be applied. The radiation synovectomy is a plausible technique of replacing surgical synovectomy, and it is a method capable of easy removal of inflamed region of synovium by beta-radiation through the direct injection with radioactive materials labelled with β-emitting radionuclide. The radiation synovectomy has merits of a simple operation and no post-operative complication.

In a treatment of cancers or arthritis by radiation emitted from radioactive materials in the lesions, the administered radioactive materials to the lesion should be retained only in the lesion and not leaked from the lesion.

If the administered radioactive materials into the lesion is leaked out of the lesion, the radioactive materials will be spread to the whole body through the blood flow, and to be accumulated in other tissues especially bone marrows, and that results in fatal damage.

In the internal radiation therapy, the administered radioactive materials should be retained in the lesion, and for this purpose, radionuclides are used in combination with carriers.

A carrier will be ideal in the proviso that carrier has a high affinity with radionuclides in vivo and in vitro, that it can be evenly distributed in the lesion, that it can be absorbed without inflammation in the lesion, that its half-life time is longer than that of radionuclide, and that it can be decomposed and excreted after decay of radionuclide.

In order to develop an ideal radioactive materials, there were some techniques proposed.

First, there was a report related to the sustained-releasing radioactive materials obtained by suspending $^{131}$I in high viscous lipiodol.

But $^{131}$I suspended in lipiodol has not been used widely on the ground that the damage to other organs or tissues by relatively high energy γ-rays emitted along with β-rays can be caused and the $^{131}$I in lipiodol infused into hepatic artery may be accumulated especially in lungs in large quantity.

Then, colloidal Y-90(Yttrium 90) or Au-198(Gold 198) has been developed.

In this case, there is a problem that normal tissue can be damaged, because radioactive materials leak cut of the lesion, as particle size is too small to be retained in the lesion. In addition, they emitted high energy γ-rays of relatively long half-life time [Fellinger et al., Weinz Inn. Med., 33, 351 (1952)].

It has been reported that resin [Turner et al., Nucl. Med. Comm., 15, 545(1994)], ceramic, and glass beads can be used as a carrier [Andrews et al., J. Nucl. Med., 35, 1637(1994)].

Since they are non-degradable, they do not leak, but there remains a problem that they are not excreted from the body after decay of radionuclide.

$^{165}$DY-FHMA($^{165}$Dysdysprosium Ferric Hydroxide Macroaggregates) , $^{165}$Dysprosium particles contained in Ferric Hydroxide Macroaggregates, has been developed [Harling et al., Nucl. Sci. and Eng., 110, 344(1992)]. But there is a problem that the procedures for preparation are complicated and the iron can be accumulated in the body.

Recently $^{165}$Dy-HMA(Dysprosium Hydroxide Macroaggregate), $^{165}$Dysprosium particles not containing iron, has been developed [McLaren et al., Eur. J. Nucl. Med., 16, 627(1990)].

But there is a limit in using $^{165}$Dy-HMA, since $^{165}$Dy-HMA is produced by irradiating stable $^{164}$Dy with neutron in the nuclear reactor. That is, its half-life time is too short for hospitals far from nuclear reactor to use it.

Particles containing $^{153}$Sm, $^{165}$Dy, $^{166}$Ho, $^{90}$Y in silicate bead with alkaline metals has been developed [U.S. Pat. No. 5,011,797]. $^{166}$Ho microspheric particles produced by irradiating with neutron in the nuclear reactor after obtaining $^{165}$Ho microspheric particles in size of 1–15 μm from the mixture of poly-L-lactic acid, polyvinyl alcohol, acetyl lactone and chloroform [J. Nucl. Med., 33, 398 (1992)]. But there is a problem that polymer can be decomposed during neutron-irradiation in the nuclear reactor and the procedure of preparation are complicated.

In addition, biodegradable and biocompatible particles of $^{153}$Sm-Hydroxyapatite have been developed.

But there is a problem that they can not be evenly distributed in the lesion and can be remained in the injector when administering to the patient, because they are in the state of particles, not in the state of solution.

As known from the above-mentioned cases, radioactive materials administered to the lesion for internal radiation therapy should not leak from the lesion.

To minimize the leakage of administered radioactive materials from the lesion, first the colloidal materials such as $^{198}$Au, and then macroaggregate have been developed; the solution has never been used.

But in the view of even distribution in the lesion, the distribution is in the order of solution > colloid > particle, and solution is the most excellent.

In other words, in case of using particles, the particles can not be evenly distributed; and so the therapeutic effect is not good; if more particles are distributed in some part, there will be over irradiated and if less particles are distributed in other part, the amount of irradiation will be below the effective dose.

As the required amount of irradiation is different according to diseases, the size of particles should be controlled in order to satisfy the required amount.

For instance, the optimum size for treating a hepatoma is 15–40 μm and for rheumatoid arthritis is 1–5 μm. But it is difficult to produce particles in optimum sizes, since a complicated procedure can not be applied on account of a problem that workers may be irradiated.

And there may remain particles, after injecting particles to patients.

Even though we can see many problems in using particles as shown above, particles have been used and solution has never been used, because it is the most important point in internal radiation therapy that the administered radioactive materials should not leak from the lesion.

As a result of the extensive study, the inventors of the present invention solved the particle's problem and the solution's problem by inventing radioactive chitosan complex.

SUMMARY OF INVENTION

Radioactive chitosan complex is a new internal radiation therapeutic agent; it exists in solution state in acidic pH and it exists in gel state in pH of the human body.

That is, it exists in solution state in acid to compensate particle's problem, and after administering to the lesion, it exists in gel state and it does not leak from the lesion.

And radioactive chitosan complex is a natural biocompatible and biodegradable product which can be excreted after decay.

In addition, it is evident that radioactive chitosan complex of the present invention can be used in the particle form as used hitherto.

In addition, the radioactive chitosan complex of the present invention can be used in a kit, wherein the radionuclide solution and lyophilized chitosan which are prepared in advance, respectively, are mixed before administering to the patient.

The object of the present invention is to provide a new radioactive chitosan complex, radioactive chitosan complex macroaggregate and a kit for preparing radioactive chitosan complex, process for preparation thereof and the use thereof for internal radiation therapy.

DETAILED DESCRIPTION OF INVENTION

The present invention will be explained in detail in the following.

I. Radioactive Chitosan Complex Radioactive materials for internal radiation therapy should be retained in the lesion, and excreted after decay For this purpose, radionuclides are used in combination with carriers. In this case, the affinity of radionuclide with carrier and sizes thereof are important.

In the present invention, chitosan which has an excellent biocompatibility and biodegradability is used as a carrier of radionuclide.

Chitosan can be easily obtained by hydrolysis of chitin, polysaccharide of N-acetyl glucosamine in β(1–4) bonding, abundant in shells of lobster, crabs, shrimp and oysters or the like.

Chitosan, a polymer of 2-deoxy-2-amino-D-glucose obtained by deacetylating of acetamide of chitin, forms chelate with heavy metals, and so it is reported that chitosan can be used as an agent of removing heavy metals (U.S. Pat. No. 5,336,415) and an agent of sustained-releasing drug.

Such characteristics are attributed to free amines of chitosan, which form chelate with metallic cation and the binding affinity of chitosan is higher than that of chitin.

Chitosan known as an edible non-toxic product can be used as a biodegradable suture silk, since it is biodegradable, and it can be used as artificial renal membrane and protective membrane for burned skin, since it has an anti-ulcer activity and antitumor activity [Kubota et al., Chem. Soc. Jpn., 66, 1807 (1993)].

The most important characteristic of chitosan is that chitosan exists in solution in acidic pH and changes into gel and into particles in higher pH.

In the present invention, radioactive chitosan complex solution and radioactive chitosan complex macroaggregate have been developed by utilizing the above-mentioned characteristics.

The molecular weight of chitosan which can be used in the present invention is 100,000–1,000,000.

The preferable molecular weight of chitosan is 200,000–800,000.

The most preferable molecular weight of chitosan is 300,000–500,000.

The molecular weight of chitosan can be changed in the range of thousands to millions according to the ratio of 2-deoxy-2-amino glucose unit and 2-deoxy-2-acetamido glucose unit obtained by hydrolysis of chitin.

The higher molecular weight is, the higher viscosity is.

Chitosan which can be used in the present invention contains the derivatives of chitosan, such as S-derivatives and P-derivatives.

The radionuclide which can be used in the present invention can contain any radionuclide which can be used for treatment of the human diseases including β-ray emitter. Radionuclide in the present invention can contain β-ray emitter, γ-ray emitter, or a radionuclide which can emit β-ray along with γ-ray.

The preferable radionuclide is a β-ray emitter, such as $^{198}$Au, $^{90}$Y, $^{186}$Re, $^{32}$P, $^{169}$Er, $^{166}$Ho, $^{153}$Sm, $^{165}$Dy which can be chosen according to the purpose of treatment. $^{198}$Au, emits also high energy γ-rays along with β-rays, and has a relatively long half-life time of 2.7 days. $^{32}$P and $^{90}$Y emit β-rays, not γ-rays and have a relatively long half-life time.

$^{165}$Dy, $^{166}$Ho, $^{153}$Sm and $^{169}$Er emit low energy γ-rays along with high energy β-rays, and have a moderate half-life time.

Of these β-emitters, Lanthane radionuclides such as $^{165}$Dy, $^{166}$Ho, $^{153}$Sm and $^{169}$Er are the most suitable for internal radiation therapy, since they emit high energy β-rays along with low energy γ-rays by which radionuclide administered into the body can be easily detected.

II. Preparation of Radioactive Chitosan Complex

In the present invention, radioactive chitosan complex, the new internal radiation therapeutic agent, can be prepared by labelling chitosan with radionuclides.

The preparation of radioactive chitosan complex will be explained in detail in the followings.

Radioactive chitosan complex can be prepared by adding radionuclide solution to chitosan solution.

Chitosan solution can be easily prepared by dissolving it in acidic solution, since chitosan is soluble in acidic environment and insoluble in alkaline environment.

The preferable acid which can be chosen from acids well known to those skilled in the art including carboxylic acid, such as acetic acid or formic acid.

Since radionuclide which can be used in the present invention should be soluble in water, soluble radionuclide nitrate or chloride such as $^{165}$Dy(NO$_3$)$_3$, $^{166}$Ho(NO$_3$)$_3$, $^{165}$DyCl$_3$ or $^{166}$HoCl$_3$ can be used.

As shown in the above, radionuclide solution may be made by dissolving the radionuclide which may be prepared by irradiating oxide or nitrate of stable nuclide such as $^{164}$Dy and $^{165}$Ho with neutron in the nuclear reactor. HCl was added to the radioactive oxide to convert into the radioactive chloride and then the resultant radioactive chloride can be dissolved in water.

The radioactive chitosan solution can be prepared by admixing said radionuclide solution and chitosan solution made by dissolving chitosan in acid.

In comparison with the known method in which macroaggregates should be made from the radioactive isotope, such a new method has advantage that workers can be protected from irradiation and the decomposition of carriers by neutron irradiation can be prevented.

In the following, the factors affecting on the preparation for chitosan complex, such as pH of reaction mixture, time of reaction, concentration of chitosan, concentration of radionuclides, and viscosity of chitosan, will be explained.

In experiments, $^{166}$Ho was used as radionuclide and Instant Thin Layer Chromatography (ITLC) was conducted with Silicic Acid (ITLC-SA). When developing solution is MeOH:H$_2$O:acetic acid (49:49:2), Rf value for Holmium is 0.8~1.0, and Rf value for Ho-chitosan complex is 0.2~0.4.

<Experiment 1> pH of Reaction Mixture for $^{166}$Ho-chitosan Complex Formation

This experiment was conducted in order to find optimal pH where chitosan forms chelate with radionuclide Chitosan solution was made by dissolving 30 mg of chitosan in 4 ml of 1% acetic acid. 0.5N HCl or 0.5N NaOH were added to adjust pH of solution of chitosan, pH 1.47, 2.00, 2.78, 3.53, 4.03, 5.00 and 6.00, respectively. 0.1 ml of 10% $^{166}$Ho(NO$_3$)$_3$·5H$_2$O was added to chitosan solution and stirred and maintained for 30 minutes.

TABLE 1

| pH of reaction mixture | yield of labelling |
| --- | --- |
| 1.47 | 20 |
| 2.00 | 30 |
| 2.78 | 95 |
| 3.53 | 95 |
| 4.03 | 30 |
| 5.00 | 20 |
| 6.00 | — |

As known in Table 1, the labelling yield of radionuclide is dependent on pH of labelling chitosan solution.

The labelled yield was more than 99% at pH 2.5~3.5, and 20-30% below pH 2.5 or over pH 3.5, where holmium almost remained without forming chelate.

And chitosan solution was changed to gel state above pH 6.0.

Therefore a preferable pH for forming chelate is 2.0~4.0. More preferable pH is 2.5~3.5.

<Experiment 2> Reaction Time for $^{166}$Ho-chitosan Complex Formation 0.1 ml(3.74 mg) of 10% $^{166}$Ho(NO$_3$)$_3$·5H$_2$O was added to solution of chitosan (30 mg/4 ml) adjusted to pH 3.0 and stirred. The samples were taken at 5, 10, 20, 30, 60 minutes, and the yield of labelling was determined.

TABLE 2

| Reaction time | yield of labelling (%) |
| --- | --- |
| 5 | 70 |
| 10 | >95 |
| 20 | >95 |
| 30 | >95 |
| 60 | >95 |

As known in FIG. 2, the yield of labelling is more than 95% at 10 minutes, which means the chitosan complex formation was almost completed after 10 minutes.

It shows that the formation constant of chitosan-chelate is very high, and hence chitosan complex will be formed by reacting radionuclide solution with chitosan solution for 10 minutes.

<Experiment 3> Concentration of Chitosan for $^{166}$Ho-chitosan Complex Formation Chitosan solutions adjusted to pH 3.0 of various concentrations were prepared, 4 mg/4 ml, 10 mg/4 ml, 20 mg/4 ml, 25 mg/4 ml, 30 mg/4 ml and 35 mg/4 ml respectively.

0.1 ml of 10% $^{166}$Ho(NO$_3$)$_3$·5H$_2$O was added to chitosan solution, stirred and maintained for 30 minutes.

TABLE 3

| conc. of chitosan (4 mg chitosan/4 ml HAc) | yield of labelling (%) |
| --- | --- |
| 35 | 99 |
| 30 | 95 |
| 25 | 35 |
| 20 | 20 |
| 10 | 15 |
| 4 | 15 |

As known in FIG. 3, the yield of labelling is more than 99% when 35 mg chitosan is contained in 4 ml of 1% acetic acid.

The yield of labelling is very low when chitosan less than 25 mg is contained.

Therefore, it is necessary to prepare chitosan solution of the concentration above 0.75% in order to form Ho-chitosan complex with 3.74 mg of holmium.

<Experiment 4> The Amount of Holmium for Ho-chitosan Complex Formation $^{166}$Ho(NO$_3$)$_3 \cdot$5H$_2$O of various concentrations (the amount of contained holmium: 3.74 mg, 7.48 mg, 11.22 mg, 14.96 mg, 22.44 mg, 29.92 mg) was added to chitosan solution (35 mg/4 ml), stirred and maintained for 30 minutes.

TABLE 4

| vol. of $^{166}$Ho(NO$_3$)$_3 \cdot$5H$_2$O (ml) | amount of contained $^{166}$Ho (mg) | yield of labelling (%) |
| --- | --- | --- |
| 0.1 | 3.74 | 99 |
| 0.2 | 7.48 | 99 |
| 0.3 | 11.22 | 70 |
| 0.4 | 14.96 | 66 |
| 0.6 | 22.44 | 45 |
| 0.8 | 29.92 | 17 |

As known in Table 4, the yield of labelling was more than 99% when 7.48 mg of holmium was added. When 11.22 mg of holmium was added, there were non-reacted holmium in a large amount. The ability of forming radioactive chitosan complex was more than 98% when the ratio of chitosan vs holmium was below 3.6:1 in chitosan.

Therefore a preferable ratio of chitosan vs holmium for forming Ho-chitosan complex is 1–4:1, more preferably 3–4:1.

<Experiment 5> Viscosity of Chitosan for Forming $^{166}$Ho-chitosan Complex

Chitosan solutions adjusted to pH 3.0 of various viscosities were prepared, 4 cps, 50 cps, 100 cps, 150 cps and 170 cps. 0.1 ml of 10% $^{166}$Ho(NO$_3$)$_3 \cdot$5H$_2$O was added to chitosan solution, stirred and maintained for 30 minutes.

TABLE 5

| viscosity of chitosan | yield of labelling (%) |
| --- | --- |
| 4 cps | 15 |
| 50 cps | 15 |
| 100 cps | 99 |

TABLE 5-continued

| viscosity of chitosan | yield of labelling (%) |
| --- | --- |
| 150 cps | 99 |
| 170 cps | 99 |

As known in Table 5, when the viscosity of chitosan is lower than 100 cps, holmium almost remained in the nearly non-labelled state. Preferably viscosity of chitosan is 100–200 cps and more preferably 130–170 cps.

Since the higher the viscosity is, the larger the molecular weight is, it can be said that formation of complex depends on the molecular weight.

<Experiment 6> The Stabilizer for $^{166}$Ho-chitosan Complex Formation

When $^{166}$Ho(NO$_3$)$_3 \cdot$5H$_2$O (50 mCi) was added to chitosan solution without stabilizer, the solution became diluted and more than 70% of contained holmium was separated to be free Holmium.

When gelatin was used as a stabilizer, the color of solution was changed to yellow and most of holmium was separated.

When 40 mg of ascorbic acid was used, the complex was stable over 8 hours. (radiochemical purity is above 99%)

The stability of solution with ascorbic acid was determined in the amount of 10 mg, 15 mg, 20 mg, 25 mg, 30 mg, 35 mg and 40 mg, respectively, and radiochemical purity was more than 99% when 30 mg of ascorbic acid was added.

Gentisic acid, gelatin and ascorbic acid can be used as a stabilizer of chitosan.

The preferable amount of ascorbic acid is 10–30 mg for $^{166}$Ho(NO$_3$)$_3 \cdot$5H$_2$O (50 mCi).

The more preferable amount is 15 mg.

The radioactive chitosan complex solution can be prepared by the following steps; 1) active radionuclide is prepared by irradiating stable nuclide such as $^{164}$Dy and $^{165}$Ho with neutron in the nuclear reactor 2) radionuclide solution is prepared by dissolving radionuclide in water, 3) chitosan solution is prepared and 4) the radionuclide solution and chitosan solution are mixed.

If a radioactive chitosan solution is administered into the human body, it will change into the gel form, which does not leak from the lesion, and the deposited radioactive chitosan can treat the lesion by irradiating radiation.

III. Preparation of a Kit for Preparing Radioactive Chitosan Complex Kit

Radioactive chitosan complex may be prepared as a kit which comprises radionuclide solution and chitosan solution.

Chitosan solution and radionuclide solution can be prepared and supplied independently to the patient. They can be mixed just before administering to the body, and radioactive chitosan complex will be formed in 10 minutes.

Chitosan solution can be freeze-dried and it may contain any conventional additives such as a pH-adjusting agent, an isotonizing agent (e.g. sodium chloride) and a preservative (e.g. benzyl alcohol).

Ascorbic acid can be used as the stabilizer.

The kit for preparing radioactive chitosan complex can be prepared by the following steps: 1) chitosan solution is prepared and then freeze-dried 2) radionuclide solution is prepared and then 1) and 2) are supplied to the patient. 3) freeze-dried chitosan is dissolved in distilled water and radionuclide solution is added. 4) after 10 minutes, it can be administered to the human body.

<Experiment 7> Stability of a Kit for Preparing
$^{166}$Ho-chitosan Complex The labelling yield of the radioactive chitosan complex of a kit prepared in accordance with the present invention was determined at the interval of one month for a year, and it was above 99%.

IV. Preparation of Radioactive Chitosan Complex Macroaggregate

Radioactive chitosan complex can be used in the form of macroaggregate as well as in the form of solution. Macroaggregate forms by diluting chitosan complex solution with distilled water and then by adding alkaline solution. Macroaggregate are precipitated at pH 9–10.

In this procedure, if chitosan complex solution is alkalized without diluting with distilled water, the solution forms the large lump, and hence it is difficult to obtain the fine particles.

Compound of lanthane series forms hydroxide in alkaline. But since the formation constant of chitosan solution with lanthane radionuclides is larger than that of lanthane hydroxide, the chitosan complex is very stable in alkaline solution Therefore when chitosan complex solution is alkalized, macroaggregate forms and they are very stable. The preferable alkaline is NaOH.

The preferable size of macroaggregate is 1–50 μm.

The preferable size of radioactive macroaggregates is varied according to diseases, 1~5 μm for rheumatoid arthritis and 10~40 μm for liver cancer.

Practical and presently preferred embodiments of the invention are illustratively shown in the following examples.

However, it will be appreciated that those skilled in the art, on consideration of this disclosure, may make modifications and improvements within the spirit and scope of the present invention.

<EXAMPLE 1>

Preparation of $^{166}$Ho-Chitosan Complex
1) Preparation of $^{166}$Ho(NO$_3$)$_3$·5H$_2$O solution 200 mg of $^{165}$Ho(NO$_3$)$_3$·5H$_2$O was dispensed in the polyethylene tube. It was irradiated with thermal neutron of $1.0 \times 10^{13}$ n/cm$^2$·sec for 10 minutes in the nuclear reactor and then dissolved in 2 ml of water.

2) Preparation of chitosan solution 300 mg of chitosan (molecular weight in about 500,000; Hydrolysis is about 85%) was dissolved in 40 ml of 1% acetic acid.

$^{166}$Ho-Chitosan complex solution was made by adding 0.1 ml of said $^{166}$Ho(NO$_3$)$_3$·5H$_2$O to said chitosan solution, by mixing well and by stirring at room temperature.

The yield of labelling was determined by ITLC-SA [MeOH(49):H$_2$O(49):HAc(2)] after 30 minutes. It was over 99%

<EXAMPLE 2>

Preparation of $^{153}$Sm, $^{165}$Dy, $^{169}$Er-chitosan Complex $^{153}$Sm, $^{165}$Dy, and $^{169}$Er-chitosan complex were prepared as described in Example 1, respectively.

Radiochemical purity of the mixture was determined and it was above 99%

<EXAMPLE 3>

Preparation of a Kit for Preparing $^{166}$Ho-chitosan Complex 40 mg of chitosan and 30 mg of ascorbic acid were dissolved in 4 ml of 1% acetic acid.

The pH of the solution was adjusted to pH3.0 with 0.5N HCl and filtered in sterilized state and freeze-dried.

Freeze-dried chitosan solution is kept at 4° C.

To use for patient, radioactive chitosan complex is prepared by dissolving freeze-dried chitosan in distilled water and by adding radionuclide solution.

<EXAMPLE 4>

Preparation of Chitosan Complex Macroaggregate $^{166}$Ho-Chitosan complex solution prepared by reacting 3.74 mg of $^{166}$Ho and 35 mg of chitosan as described in Example 1 was diluted with 5 volumes of water.

Stirring it vigorously, 2N NaOH was dropped to precipitate completely (pH 9–10).

The resultant suspension was sonicated for 5 minutes.

The precipitate was separated from the supernatant by centrifuging at 240×g for 3 minutes, and the resultant chitosan macroaggregates were resuspended in 4 ml of saline solution.

The suspension was dispensed into 10 ml vial, sealed and sterilized in autoclave, at 121° C. for 30 minutes.

The particles of macroaggregates was evenly diffused by retreating in sonication washer.

The sizes of particles were determined, and the average size was about 25 μm.

In-vitro stability and in-vivo stability for radioactive chitosan complex and its macroaggregate were determined and described in the following.

<EXAMPLE 5>

Examination of In-vitro Stability of $^{166}$Ho-chitosan Complex and Macroaggregate 166Ho-chitosan complex and macroaggregate containing 2 mCi of $^{166}$Ho in each vial were maintained at room temperature and 37° C. for 25 days.

The radiochemical activity was determined at every time interval with ITLC-SA[MeOH(49):H$_2$O(49):acetic acid(2)] (Referred to Table 6. 7).

The macroaggregate prepared as described in Example 4 were washed with 0.9% NaCl(5 ml) at every time interval.

The radioactivity remained in macroaggregates and in filtrate were determined (Referred to Table 8).

TABLE 6

Examination of stability at room temperature

| lapsed time (day) | Radiochemical activity of $^{166}$Ho-chitosan complex | Radiochemical activity of $^{166}$Ho-chitosan macroaggregate |
| --- | --- | --- |
| 0 | 99 | 100 |
| 2 | 99 | 100 |
| 4 | 99 | 100 |
| 6 | 99 | 100 |
| 13 | 99 | 100 |
| 25 | .99 | 100 |

TABLE 7

Examination of stability at 37° C.

| lapsed time (day) | Radiochemical activity of $^{166}$Ho-chitosan complex | Radiochemical activity of $^{166}$Ho-chitosan macroaggregate |
| --- | --- | --- |
| 0 | 99 | 100 |
| 2 | 99 | 100 |
| 4 | 99 | 100 |
| 6 | 99 | 100 |
| 13 | 99 | 100 |
| 25 | 99 | 100 |

As known in Table 6 and 7, nearly 100% of the radioactivity at Rf=0.2–0.4 of $^{166}$Ho-chitosan complex was remained and the radioactivity at Rf=0.9–1.0 of free $^{166}$Ho was negligible for 25 days.

The results indicated that in vitro stability of chitosan macroaggregate was excellent at room temperature or 37° C.

TABLE 8

Examination of stability by washing

| Vol. of washing soln. (ml) | Radiochemical activity of $^{166}$Ho macroaggregate (%) |
| --- | --- |
| 5 | 100 |
| 10 | 100 |
| 15 | 100 |
| 20 | 100 |
| 25 | 100 |
| 30 | 100 |

As known in Table 8, when $^{166}$Ho-chitosan macroaggregates were washed with saline solution, macroaggregates were not dissolved or not changed into colloidal state. And nearly 100% of the radiochemical activity was remained in the precipitate.

Regarded as the above, the free amine of chitosan combines with $^{166}$Ho so tightly to form a very stable chelate.

<EXAMPLE 6>

Examination of In Vivo Stability of $^{166}$Ho-Chitosan Complex and Macroaggregate.

The pH of $^{166}$Ho-chitosan complex solution prepared in accordance with Example 1 was adjusted to 5.5 and then filtered through 0.2 μm membrane filter and sterilized. 0.5 ml(400 μCi) of $^{166}$Ho-chitosan complex solution was administered into the knee joint of normal rabbit by intra-articular injection.

After an appropriate time interval, radioactivity remained within the knee joint was compared with the total radioactivity immediately after injection by using γ-camera.

The macroaggregate prepared in accordance with Example 4 was suspended with saline solution, and sterilized in autoclave at 121° C. for 30 minutes.

0.1 ml aliquot of this suspension was administered into the knee joint.

TABLE 9

% of radioactive chitosan complex and its macroaggregate remained in the knee joint of the normal rabbit

| lapsed time (hr) | $^{166}$Ho-chitosan complex (%) | $^{166}$Ho-chitosan Macroaggregate |
| --- | --- | --- |
| 0 | 100 | 100 |
| 2 | 99.9 | 99.9 |
| 6 | 99.8 | 99.9 |
| 24 | 99.7 | 99.8 |
| 48 | 99.6 | 99.7 |

As known in Table 9, the radioactivity was almost remained in the joint cavity after injection (excluding physical decrease of $^{166}$Ho) at 2 hours (99.9%), 6 hours (99.9%), 24 hours (99.8%) and 48 hours (99.7%) respectively.

It was confirmed that the radioactive chitosan complex and macroaggregate do not leak out of the lesion.

Regarded as the above, $^{166}$Ho-Chitosan complex and macroaggregate are very stable in vivo and in vitro. Chitosan forming chelate with holmium is a biodegradable and biocompatible material which remains absorbed in articulate for an appropriate term and degrades and excretes slowly after decaying.

That is, chitosan of which the free amines forms chelate with radionuclide is an ideal internal radiation therapeutic agent which treats the lesion in the body and then excretes out of the body.

The effect of radioactive chitosan complex as an internal radiation therapeutic agent is described in the following.

<Experiment 7> Clinical Experiment of Radioactive Chitosan Complex

1) Radiation Synovectomy

An internal radiation therapy was conducted to 36 patients selected according to standard of ACR(American College of Rheumatology).

Radioactive chitosan complex was injected into the knee joint.

The amount of injected radioactive chitosan complex was dependent on individuals, but average was 15–20 mCi.

The average observation time was 50.4 weeks.

The results were excellent in 44% of patients, good in 32%, not good in 24%, and hence 76% of patients were cured.

2) The Treatment of Liver Cancer 45 patients with liver cancer in the size of 1–3 cm were treated with 10–20 mCi of radioactive chitosan complex according to the size of cancer. 90–95% of patients showed good results. It was directly injected to the cancer tissue under ultrasonic induction.

Regarded as the above, radioactive chitosan complex and macroaggregate have a good effect for treatment of various cancers and rheumatoid arthritis.

In case of $^{166}$Ho, radioactive chitosan complex and macroaggregate can be administered in the amount of 5–15 mCi at one time, according to kinds of disease and the size of lesions. Chitosan complex solution may be directly administered by injector to the lesion. Chitosan complex macroaggregate may be administered after dissolving in H$_2$O, saline solution or ethanol.

The radioactive chitosan complex and its macroaggregate can be used as an internal radiation therapy for rheumatoid arthritis, liver cancer, brain cancer, breast cancer, ovary cancer and the like by administering directly to the lesion.

What is claimed is:

1. An internal radiation therapeutic composition which is administrable in an aqueous solution and which consists essentially of an active radionuclide directly bonded to chitosan, said composition formed such that upon contact with higher pH of physiological conditions, said aqueous solution is converted to a stiff gel form in which the active radionuclide does not migrate into surrounding healthy tissue, wherein the radionuclide is selected from the lanthanide series.

2. The internal radiation therapeutic composition according to claim 1, wherein the active radionuclide emits β rays in high energy and γ-rays in low energy.

3. The internal radiation therapeutic composition according to claim 2, wherein the active radionuclide is selected from the group comprising $^{153}$Sm, $^{165}$Dy, $^{166}$Ho and $^{169}$Er.

4. The internal radiation therapeutic composition according to claim 1, wherein the chitosan has a molecular weight of 100,000–1,000,000.

5. The internal radiation therapeutic composition according to claim 1, wherein the composition in an aqueous solution has an acidic pH.

6. Process for preparing the internal radiation therapeutic composition of claim 1 comprising
   1) irradiating a water-soluble stable radionuclide compound with neutrons in a nuclear reactor to convert the water soluble stable radionuclide compound into an active radionuclide compound;
   2) dissolving the active radionuclide compound in water to form a solution;
   3) dissolving a chitosan in acidic solution to form a chitosan solution; and
   4) adding the active radionuclide compound solution to the chitosan solution to form the internal radiation therapeutic composition.

7. Process for preparing the internal radiation therapeutic composition according to claim 6, wherein the water-soluble stable radionuclide compound is selected from the group $^{164}$Dy(NO$_3$)$_3$, $^{164}$Dy$_2$O$_3$, $^{165}$Ho(NO$_3$)$_3$ and $^{165}$Ho$_2$O$_3$.

8. An internal radiation therapeutic composition prepared according to claim 6, wherein the chitosan solution has a pH of between 2 and 4.

9. The internal radiation therapeutic composition according to claim 8, wherein the chitosan solution is an acetic acid solution.

10. An internal radiation therapeutic composition prepared according to claim 6, wherein a ratio of the water-soluble stable radionuclide compound and the chitosan is 1:1–4.

11. An internal radiation therapeutic composition prepared according to claim 6, wherein the internal radiation therapeutic composition has a viscosity of 100–200 cps.

12. The internal radiation therapeutic composition according to claim 1 which is administrable in a form of radioactive macroaggregate which comprises the active radionuclide compound and chitosan, in which the active radionuclide does not migrate into surround healthy tissue.

13. The internal radiation therapeutic composition according to claim 12, wherein the particles of the radioactive macroaggregate have a size of 1–50 μm.

14. Process for preparing the internal radiation therapeutic composition of claim 12 comprising
   1) irradiating a water-soluble stable radionuclide compound;
   2) dissolving the active radionuclide compound in distilled water to form a solution;
   3) dissolving a chitosan in acidic solution to form a chitosan solution;
   4) adding the active radionuclide compound solution to the chitosan solution to form a complex solution;
   5) diluting the complex formed in step (4) with distilled water; and
   6) adding an alkaline solution to the diluted solution formed in step (5).

15. The internal radiation therapeutic composition according to claim 1, effective against rheumatoid arthritis or cystic cancer, such as liver cancer, brain cancer, breast cancer or ovary cancer.

16. The internal radiation therapeutic composition according to claim 12, effective against rheumatoid arthritis or cystic cancer, such as liver cancer, brain cancer, breast cancer or ovary cancer.

17. The process of claim 6 wherein the water used in step (2) is distilled water.

18. The process of claim 6, wherein prior to step (4), the chitosan solution prepared in step (3) is freezed-dried and dissolved in distilled water after freeze-drying.

19. The process of claim 14, wherein prior to step (4), the chitosan solution prepared in step (3) is freezed-dried and dissolved in distilled water after freeze-drying.

* * * * *